United States Patent [19]

de Laforcade

[11] Patent Number: 4,877,026
[45] Date of Patent: Oct. 31, 1989

[54] SURGICAL APPARATUS

[75] Inventor: Hughes de Laforcade, Manchester, Mass.

[73] Assignee: Microline Inc., Danvers, Mass.

[21] Appl. No.: 223,432

[22] Filed: Jul. 22, 1988

[51] Int. Cl.$^4$ ............................................. A61B 17/32
[52] U.S. Cl. .................................. 128/305; 128/303 R; 128/318; 30/329; 604/22
[58] Field of Search .................... 128/303 R, 305, 321, 128/318; 604/22; 30/1.5, 109, 329, 335

[56] References Cited

U.S. PATENT DOCUMENTS

| | | | |
|---|---|---|---|
| 984,756 | 2/1911 | Frisch | 128/321 |
| 2,518,994 | 8/1950 | Miller | 128/321 |
| 3,828,791 | 8/1974 | Santos | 128/321 |
| 4,587,716 | 3/1981 | Sutherland | 128/318 |
| 4,674,501 | 6/1987 | Greenberg | 128/305 |

OTHER PUBLICATIONS

7 Pages of Trade Literature (undated).

Primary Examiner—Michael H. Thaler

[57] ABSTRACT

A surgical apparatus for performing a surgical procedure such as severing tissue in microsurgical operations. In the case of a cutting implement, the apparatus includes an elongated rigid housing having an inner wall and supporting therein first and second elongated shaft members. The first and second shaft members each have juxtaposed inner surfaces slidable relative to each other and outer surfaces terminating in corners which abut and are slidable relative to the inner tubular wall. The first shaft has a driven end and an active or operable cutting end having a first cutting edge disposed outside of the tubular housing. The second shaft has a fixed end and a cutting end with a second cutting edge also disposed outside of the tubular housing. Drive means are connected to the driven end of the first shaft for causing axial reciprocatory movement of the first cutting edge through a predetermined stroke distance to carry the first cutting edge past the second cutting edge to effect cutting action.

24 Claims, 4 Drawing Sheets

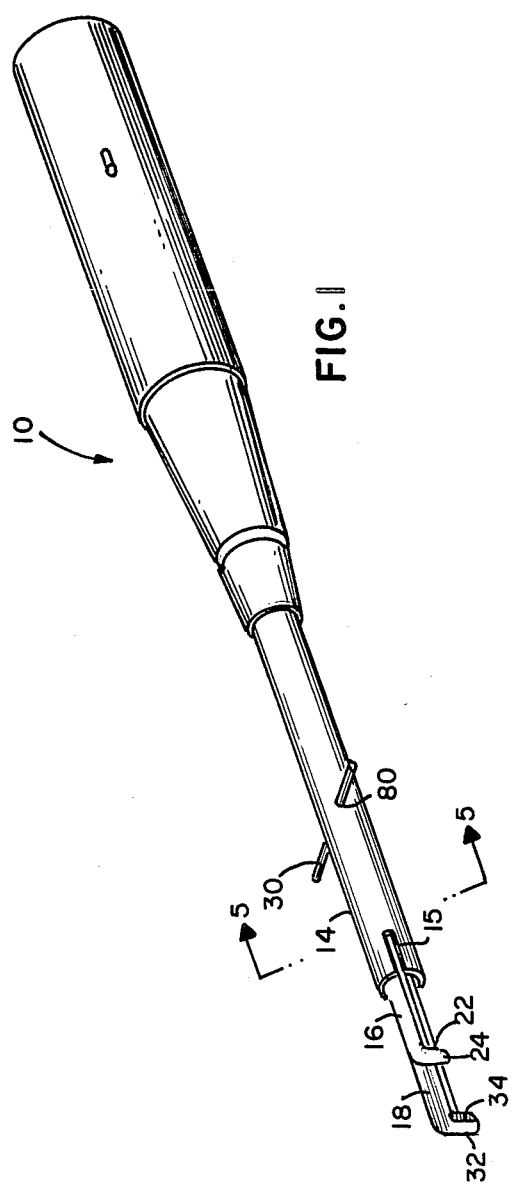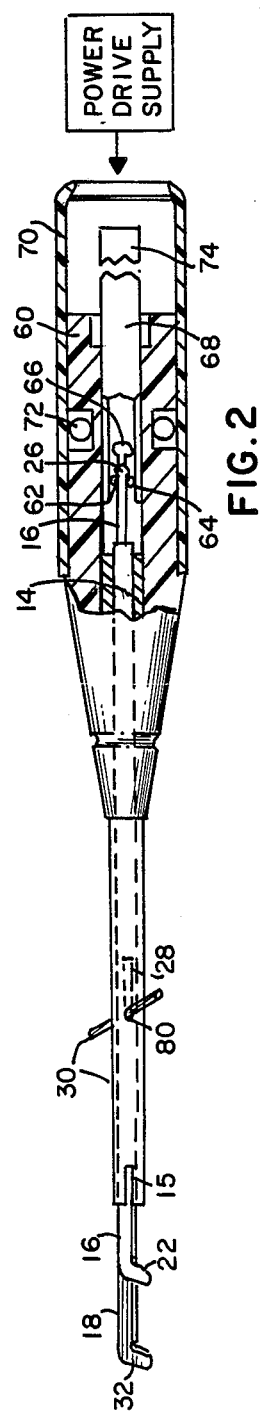

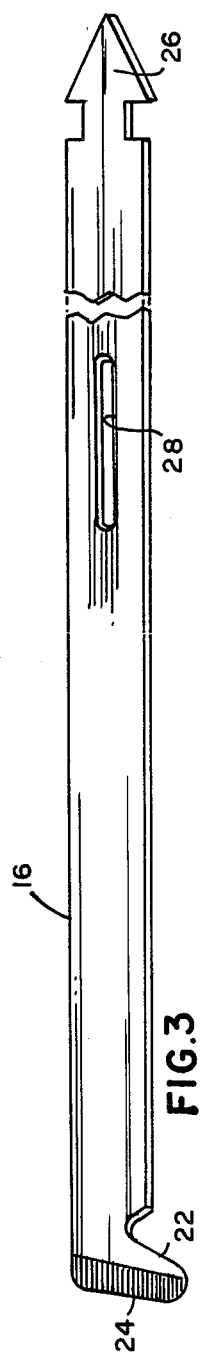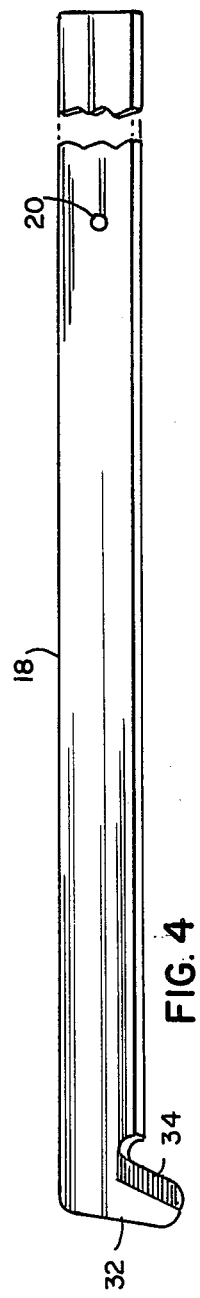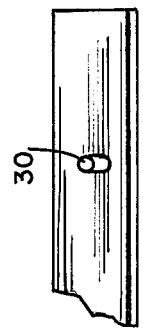

SURGICAL APPARATUS

FIELD OF THE INVENTION

The present invention relates to surgical apparatus and more particularly to a disposable ophthalmological instrument, especially a cutting instrument.

BACKGROUND OF THE INVENTION

In the prior art, a variety of different devices and instruments are disclosed which are adapted for the cutting, holding, incision and removal of tissue in a region of very limited volume, such as in parts of the eye or in regions of the nervous system. The state of the art is exemplified by the following U.S. Pat. Nos.:

| | |
|---|---|
| 3,528,425 | 4,436,091 |
| 3,844,272 | 4,530,356 |
| 4,099,529 | 4,602,630 |
| 4,320,761 | 4,672,965 |
| 4,368,734 | 4,689,040 |

While such prior art devices provide improvements in the areas intended, there is still a great need for a microsurgical cutting apparatus which is relatively inexpensive to manufacture, is of simple construction and provides great precision in operation. Especially, there is a need for apparatus that can be discarded after a single procedure without incurring inordinate expense.

In general, most of the surgical apparatus presently available are extremely expensive to design and fabricate and become dull fairly quickly, usually after only a few uses. Surgeons using such devices have had to have the cutting edges sharpened. They have found that frequently such sharpened cutting edges do not provide adequate cutting after sharpening. Thus, a surgical apparatus that is reliably sharp, inexpensive to produce and disposable is highly advantageous in the art.

Accordingly, a principal object of the present invention is to provide a microsurgical cutting apparatus which is compact, efficient, relatively inexpensive and disposable.

Another object of the present invention is to provide a microsurgical cutting apparatus that has a unique geometry of the shafts.

Another object of the present invention is to provide an improved apparatus to be inserted in an incision in the eye so that a variety of accessory instruments can be introduced into the eye also to form a variety of surgical techniques.

A still further object of the present invention is to provide an improved cutting apparatus and a method of fabricating such devices.

These and other desirable objects, features and advantages of the present invention will become apparent to those skilled in the art upon reading the following specifications when taken in conjunction with the accompanying drawings and the appended claims.

SUMMARY OF THE INVENTION

The present invention provides for an improved surgical apparatus for performing surgical procedures particularly the manipulation or severing tissues in ophthalmological microsurgery. The apparatus generally comprise an elongated rigid tubular housing having an inner wall and supporting therein a first and a second elongated shaft member. The first and second elongated shaft members each have inner surfaces juxtaposed and slidable relative to each other, and have outer surfaces which terminate in corners that abut the inner tubular wall, whereby the shaft members are held in the tubular housing. The first elongated shaft member is provided with a driven end and an active or operable end that forms a surgical implement, for example, a cutting edge or a one half of a pair of forceps. The second elongated shaft member is immobile within the tubular housing and has a fixed end and an active or operable end that forms a surgical implement such as another cutting edge or the other forcep which co-act with the respective active end of the first elongated shaft member. In one embodiment, the cutting edges of the first and the second shaft members are disposed at an angle to a plane perpendicular to the longitudinal axis of the tubular housing and provide a vertical cutting action relative to each other. In another embodiment, one of the cutting edges is pivotably attached to the first shaft member whereby retraction of the first shaft member into the tubular member causes the cutting edge to urge against the mouth of the tubular housing and rotate it about an axis normal to the axis of the tubular housing. Such rotation causes the first cutting edge to engage the second cutting edge whereby tissue cutting can occur.

The first elongated shaft member is actuated relative to the second shaft member by a drive means connected to the driven end of the first shaft member for causing axial reciprocatory movement of the first cutting edge through a predetermined stroke distance to carry the first cutting edge past the second cutting edge and provide a cutting action by the cooperation of the cutting edges.

The first elongated shaft member may be reciprocated by means of a piston attached to a tang disposed on the driven end which may be operated manually or with a motor mounted in a handle housing which is small enough so they can be hand held and is preferably powered by a self-contained power source but may be powered by an external power source.

In the manufacture of the elongated shaft members and their associated active ends, they are preferably prepared by well known photochemical etching processes in which the shape of the shaft members are masked on a sheet of steel and the unmasked portions are chemically dissolved to produce the shaft members and their active ends of the shape dictated by the mask. The shaft members are then removed from the substrate and separated from a flashing that links them together. They are then honed to a finished edge by any well known honing operations.

BRIEF DESCRIPTION OF THE DRAWINGS

For a fuller understanding of the nature and desired objects of the present invention, reference should be made to the following detailed description taken in conjunction with the accompanying drawings wherein like reference characters denote corresponding parts throughout several views and wherein:

FIG. 1 is a perspective view, partially shown in phantom lines of one form of the surgical apparatus employing the present invention;

FIG. 2 is an enlarged fragmentary view, partially in cross-section of the surgical apparatus of FIG. 1;

FIGS. 3 and 4 are enlarged perspective views of one embodiment of elongated cutting members in accordance with one embodiment of the present invention;

FIG. 4A is an enlarged fragmentary view of an alternative embodiment of the fixed end of the cutting member of FIG. 4;

DETAILED DESCRIPTION OF THE PREFERRED EMBODIMENT

Figure 5:
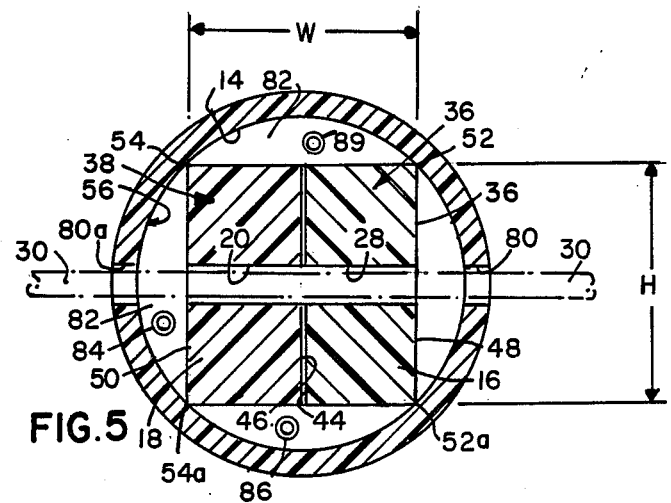
FIG. 5 is an enlarged cross-sectional view taken substantially along the line 5—5 of FIG. 1.

Referring now to the drawings, and more especially to FIGS. 1-5, a surgical device indicated generally by the numeral 10 is illustrated employing an embodiment of the surgical apparatus in accordance with the present invention. The device shown is useful for severing or cutting tissue in microsurgical operations.

The surgical apparatus 10 comprises an elongated rigid tubular housing 14. The tubular housing 14 can be formed of a suitable metal including alloys such as "304 stainless steel" having, for example, a length of 2 inches and an inside diameter of 0.025 inches and an outside diameter of 0.035 inches. A recess 15 is cut into the end of the tubular housing 14 to receive at least a portion of the cutting end 22 whereby to aid in centering of the device during assembly and to provide support during operation.

The operative mechanism includes a first elongated shaft member 16 and a second elongated shaft member 18. The first shaft member 16 and the second elongated shaft member 18 each extend inside of tubular housing member 14. Exemplary of the surgical implements that can be disposed at the end of the shaft members is a cutting end 22 with a cutting edge 24. A tang 26 (shown in FIG. 3) is disposed at the end opposite the cutting end 22 and is used to engage a driving mechanism. The first elongated shaft member 16 is also provided with slot 28 (shown in phantom lines in FIG. 2), which dictates the length of travel (stroke distance) of the cutting end 22.

A pin 30, FIG. 4A (frequently in the form of a length of wire shown in phantom lines in FIG. 1) limits the distance that shaft 16 can travel during its reciprocatory cutting movement as will be discussed hereinafter. The second elongated shaft member 18 terminates (at one end) with a cutting end 32 having a cutting edge 34. The second shaft member 18 is fixedly disposed in tubular housing 14 by pin 30 which passes through hole 20 and holes 80 and 80a in the tubular housing 14 when the pin 30 is in the form of a wire.

The shaft members 16 and 18 each have a generally rectangular cross-sectional area 36 and 38 so that when inserted in tubular housing 14 (as best seen in FIG. 5), the inner surfaces 44 and 46 respectively, are juxtaposed and slidable relative to each other. The width W of the shaft members 16 and 18 is the same at the top and the bottom, and the height H of the outer surfaces 48 and 50 are preferably the same on both sides so that the corners 52 and 52A of shaft member 16 and corners 54 and 54a of shaft member 18 abut inner wall 56 of tubular housing 14. In this manner, the shaft members 16 and 18 are held in spatial relationship within the tubular housing 14. Additionally, elongated shaft member 16 (which is arranged for reciprocatory movement relative to elongated shaft member 18) is guided in its reciprocatory movement as well as maintained in the juxtaposed slidable relationship with the inner surface 46 of shaft member 18 by the abutting contact of corners 52 and 52a with the inner wall 56 of the tubular housing 14.

In a typical example, the width of each shaft member 16 and 18 was 0.008 inch with a height of 0.02 inch. The inner diameter of the tubular housing 14 is 0.0265 inch. The typical overall length of movable shaft member 16 is about 1.7 inches while the fixed shaft member 18 is slightly shorter at about 1.4 inches. Additionally, the slot 28 is typically about 1 mm. in length whereby the reciprocatory stroke distance of the first shaft member 16 is limited to the 1mm. stroke distance in each direction.

Referring now more particularly to FIG. 2, it can be seen that the tubular housing 14 containing the elongated shaft members 16 and 18 is inserted into inner handle housing 60 with sufficient force to insert the tang 26 of shaft member 16 between two pairs of wires 62 and 64 that are attached at the end of a resilient Y-shaped coupling 66 disposed at one end of rod 68. An outer handle housing 70 is slidable over the inner handle housing 60 and held in position by O-ring 72.

The first elongated shaft member 16 may be axially reciprocated within tubular housing 14 by connecting the other end 74 of rod 68 to a suitable drive means (not shown). Various drive means can be employed such as a reciprocatory piston driven by an electric, pneumatic or hydraulic power supply.

Figure 6:
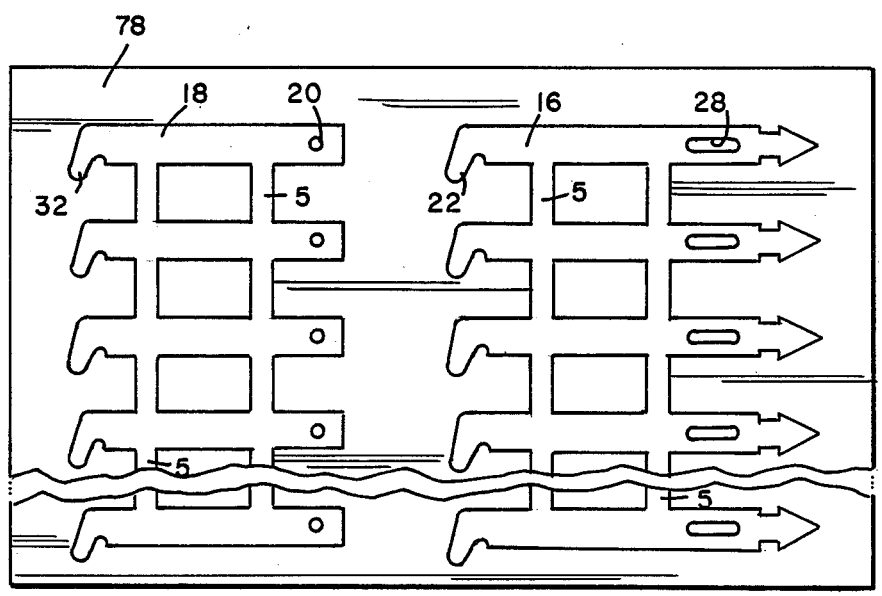
FIG. 6 is a schematic representation of a metal sheet having a photosensitive coating thereon and images of the shaft members thereon illustrating part of the photochemical process for making the shafts in accordance with the present invention.

As previously mentioned, the shaft members are preferably formed by a photochemical machining process. In accordance with the photochemical machining process, a master drawing is made of the shaft members 16 and 18 which may be up to fifty times the size of each shaft member, depending upon the tolerance required. Thereafter, multiple negatives containing a plurality of each shaft image are produced on a photorepeating machine. A steel sheet 76 as shown in FIG. 6, has printed on its surface a plurality of the shaft images of the shaft members 16 and 18, with the operating instrumentalities disposed at the end thereof. The sheet 76 is coated with a photosensitive coating 78. Photographic reductions to the actual size of the apparatus and a final step produces a film master that is the exact size of the finished shaft members. The film master is then etched to remove all metal not protected by the coating applied during a developing process. This step leaves the finished shaft members 16 and 18 joined together by flashings 5. The advantages of employing the foregoing photochemical machining process for preparing the shaft members of the present invention is that it provides for low cost, and the integrity of the metal is unchanged as may occur with other processes which affect hardness, grain structure and ductility. The process also provides for a multiplicity of the shaft members with their respective operating instrumentalities. Each such shaft member is interchangeable and readily adaptable to disposition within the tubular member 14.

After the photochemical etching operation, the shaft members 16 and 18 are stripped from the plate 76 and the flashings 5 removed. Since the elongated shaft members are of a single and uniform thickness throughout their body, including their operative end, when the operative ends include cutting edges, each cutting edge must be sharpened to provide the cutting edges that are necessary for the device of the present invention. Conventional honing techniques produce such sharpening.

Referring now more particularly to FIGS. 1 and 3 to 5, a pin (wire) 30 extends through holes 80 and 80a in tubular member 14, slot 28 and hole 20 (FIG. 4). The diameter of pin 30 is substantially the same as the width of slot 28 whereby shaft 16 may be controlled in its lateral movement and limited in its stroke by their respective widths and lengths. In operation, the first shaft member 16 is actuated by the drive means illustrated symbolically in FIG. 2. The drive means imparts axial reciprocatory movement to the first shaft member 16 through a predetermined stroke distance, the distance of which is determined by the length of slot 28.

The reciprocatory movement of shaft 16 causes a corresponding axial reciprocation of the first cutting edge 24 past the second cutting edge 32 of the respective shaft members to provide a cutting action by coacting cutting edges 24 and 32 to encounter and sever tissue engaged by the cutting edges.

Referring again to FIG. 5, there is shown another feature of the present invention. As shown, the construction and arrangement of the shaft members 16 and 18 within the tubular housing 14 provides for free board spaces 82 defined between the shaft member surfaces and the inner wall surface 56 of the tubular member 14. The free board spaces 82 can provide suitable conduits for the introduction into the work area of a variety of accessory instrumentations that may be used for surgical procedures. For example, a fluid conduit 84 for irrigation fluids can be provided, as well as fiber optic member 86 for lighting, or a suction conduit 89 for removing debris, all of which can be connected to respective suitable supply and power sources (not shown).

Figure 7A:
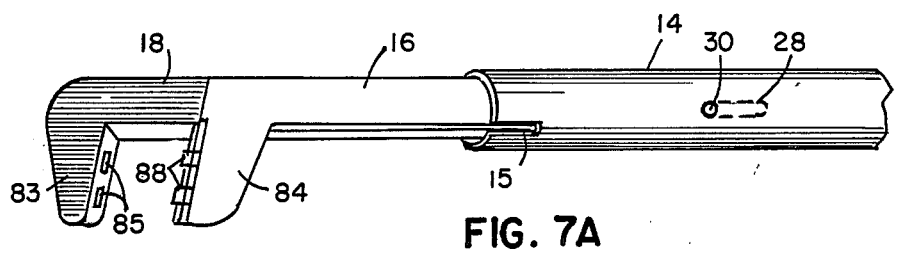
FIGS. 7A to 7C are enlarged fragmentary views of different types of active ends of the surgical apparatus in accordance with the present invention.
Figure 7B:
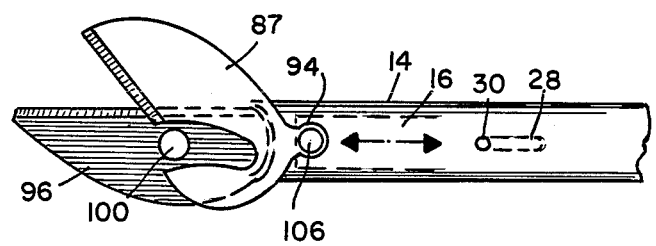

Referring to FIGS. 7a and 7b, there are shown modified embodiments of the active or operable ends of the elongated shaft members 16 and 18.

In the embodiment shown in FIG. 7a, the active end members 83 and 84 provide a forcep action when the reciprocatory action of shaft member 16 causes teeth 88 of end 84 to engage slots 85 formed in the end 86.

In the embodiment shown in 7b, the active end of shaft 16 has a shaft member 87 with a cutting edge 90 and an arcuate groove 92. The shaft member 87 rotates by means of a ball socket 94 disposed at the end of shaft member 16. The active end of shaft member 18 is provided with a blade 96 having a cutting edge 98 and a groove guide stud or pin 100. When the shaft member 16 is reciprocated, the blade member 88 moves up and down (as shown by the arrow) to provide a cutting or scissors action with blade 96.

Figure 7C:
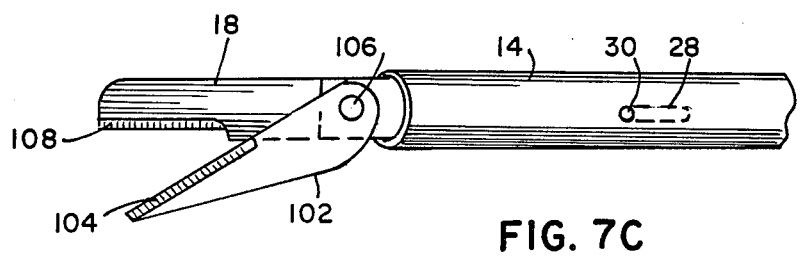

Referring to FIG. 7c, a different embodiment of the active end of the shaft members is shown. The first shaft member 16 has an active end comprising a blade member 102 with a cutting edge 104. The blade member 102 rotates about a stud 106 and is free to move in a 360° arc. The second shaft member 18 has an active end a cutting edge 108 which is disposed on a plane that is parallel to the axis of the tubular member 14. Shafts 16 and 18 are mounted inside of the tubular member 14 in a manner similar to that shown in FIG. 5. When shaft member 16 is retracted, blade member 102 will engage the mouth of tubular member 14 and cause it to swing up whereby its cutting edge 104 will engage the cutting edge 108 of the second shaft member 18. Upon extension of shaft 16 from tubular member 14, blade member 102 will drop down and disengage from cutting edge 108.

It is apparent that changes and modifications can be made within the spirit and scope of the present invention which provides for an improved microsurgical cutting apparatus and a method of fabricating the same.

While the invention has been described with respect to preferred embodiments, it is apparent to those skilled in the art that changes and modifications can be made without departing from the scope of the invention herein involved in its broader aspects. Accordingly, it is intended that all matter contained in the above description, or shown in the accompanying drawings, shall be interpreted as illustrative and not in a limiting sense.

As my invention, I claim:

1. A surgical apparatus for insertion into the eye for surgical procedures, said apparatus comprising:

an elongated rigid tubular housing of circular cross section having an inner tubular wall supporting therein a first and a second elongated shaft member;

said first and said second elongated shaft members each having juxtaposed inner surfaces slidable relative to each other for a predetermined stroke distance, said first and said second shaft members further having outer surfaces terminating in corners, said corners abutting said inner tubular wall, said shaft members being held in a spacial relationship relative to each other and said inner tubular wall by said corners, whereby said shaft members occupy only a portion of the space in said inner tubular housing, thus leaving a freeboard space between said outer surfaces and the inner tubular wall;

said first shaft member having at one end, a driven end, and at the other end a first operable means disposed thereon;

said second shaft member being fixedly disposed in said tubular housing and having a second operable means disposed thereon, said second operable means being cooperatable with said first operable means to perform a surgical procedure; and means for restraining the motion of said first shaft member on a plane parallel to the axis of said tubular housing and for limiting the distance of a stroke of said first shaft member relative to said second shaft member, whereby to limit the movement of said first operable means relative to said second operable means.

2. The surgical apparatus according to claim 1 wherein the means for limiting the distance of the stroke of said first shaft member includes at least one slot disposed in said first shaft member.

3. The surgical apparatus according to claim 2 wherein the means for limiting the distance of the stroke further includes a hole disposed in said second shaft member, and means disposed in said hole and said slot to limit said stroke distance.

4. The surgical apparatus according to claim 3 wherein the means for limiting the distance of a stroke further includes an aperture in at least one wall of said tubular housing and means passing through said aperture, said slot, and said hole to restrain the movement of said first shaft member relative to said tubular housing and limit the stroke distance of the first shaft member to the length of said slot.

5. The surgical apparatus according to claim 4 wherein the means for limiting the distance of a stroke further includes a second aperture disposed in the wall of said tubular housing, said second aperture being disposed opposite the first aperture in the wall of said tubular housing.

6. The surgical apparatus according to claim 4 wherein the stroke limiting means is a length of wire having a diameter substantially equivalent to said aperture.

7. The surgical apparatus according to claim 4 wherein the diameter of the aperture in the wall of the tubular housing, the hole in the second shaft member, and the width of the slot in the first shaft member are substantially equal.

8. The surgical apparatus according to claim 1 further including recess means disposed at the end of said tubular housing nearest the operable means, whereby to receive a portion of the first operable means therein.

9. The surgical apparatus according to claim 8 wherein the recess means is a slot in said tubular member, said slot being disposed parallel to the axis of said tubular member, whereby said first operable means can be seated in said slot to center the first and the second elongated shaft members during assembly of the apparatus, and further whereby to give support to said first operable means during use of said apparatus.

10. The surgical apparatus according to claim 1 wherein the first and the second operable means are scissors including first and second cutting members having opposed cutting edges.

11. The surgical apparatus according to claim 10 wherein said cutting edges of said first and said second cutting members are at an angle to a plane perpendicular to the longitudinal axis of said tubular housing.

12. The surgical apparatus according to claim 11 wherein the cutting edge of said first cutting member is at an angle to the plane of the cutting edge of the second cutting member.

13. The surgical apparatus according to claim 1 wherein each of the first and second shaft members have a generally rectangular cross-sectional shape, and said first shaft member is slidable on a plane parallel to the axis of said tubular housing.

14. The surgical apparatus according to claim 1 wherein the first operable means includes a cutting edge pivotably disposed on the end of said first shaft member, the axis of rotation of said cutting edge being normal to the axis of said rigid tubular housing, the stroke of said first shaft member being such that the pivot point is disposed inside of said rigid tubular housing when extended and also when retracted, whereby to rotate said cutting edge of said first operable means upon retraction of said first shaft member, and said second operable means also includes a cutting edge, whereby to provide engagement of said first cutting edge with said second cutting edge upon movement of said first shaft member.

15. The surgical apparatus according to claim 14 wherein the operable means is attached to said first shaft member by a round end disposed on said operable means, said round end being disposed in a socket disposed on said first shaft member.

16. The surgical apparatus according to claim 1 wherein the first and the second operable means are forceps including first and second mating gripping members.

17. The surgical apparatus according to claim 1 wherein the operable means are forceps.

18. The surgical apparatus according to claim 1 further including drive means connected to said driven end of said first shaft member for causing axial reciprocatory movement of said first operable means through a predetermined stroke distance to carry said first operable means into a cooperative relationship with said second operable means.

19. The surgical apparatus according to claim 1 further comprising a handle housing including and means for releasably attaching said tubular housing to said handle housing.

20. The surgical apparatus according to claim 19 wherein the driven end of the first shaft member terminates in a tang member and said handle housing further includes spring clip means to engage said tang member.

21. The surgical apparatus according to claim 1 wherein said tube encloses substantially the entire length of said shafts, and terminates adjacent said operable means.

22. A surgical apparatus for insertion into the eye for surgical procedures, said apparatus comprising:
an elongated rigid tubular housing of circular cross section having an inner tubular wall and supporting therein a first and a second elongated shaft member;
said first and said second elongated shaft member each having juxtaposed inner surfaces slidable relative to each other for a predetermined stroke distance, said first and said second shaft members further having outer surfaces terminating in corners abutting said inner tubular wall, said shaft members being held in a spacial relationship relative to each other and said walls by said corners, whereby said shaft members occupy only a portion of the interior of said tubular member and leave freeboard space between the outer surfaces and said inner tubular wall;
said first shaft member having at one end, a driven end and a first operable means disposed on the other end;
said second shaft member being fixedly disposed in said tubular housing and having a second operable means disposed thereon, said second operable means being cooperatable with said first operable means to perform a surgical procedure;
means for limiting the distance of a stroke of said first shaft member including at least one slot disposed in said first shaft member, a hole disposed in said second shaft member and an aperture in at least one wall of said tubular housing, and means passing through said aperture, said slot and said hole to restrain the movement of said first shaft member relative to said tubular housing and limit the stroke distance of the first shaft member to the length of said slot.

23. The surgical apparatus according to claim 22 wherein the corners of the outer surface of said first shaft member are in substantially continuous abutting contact with the inner tubular wall during reciprocatory movement whereby the inner surface of said first shaft member is maintained in juxtaposed slidable relationship with the inner surface of said second shaft member so as to effect a cooperative action of said first and second operable members.

24. The surgical apparatus according to claim 22 wherein said tube encloses substantially the entire length of said shafts, and terminates adjacent said operable means.

* * * * *